US000001968H

(19) United States

(12) Statutory Invention Registration (10) Reg. No.: US H1968 H

Bernstein (43) Published: Jun. 5, 2001

(54) HYPERPOLARIZED MR IMAGING USING PULSE SEQUENCE WITH PROGRESSIVELY INCREASING FLIP ANGLE

(75) Inventor: Matthew A. Bernstein, Waukesha, WI (US)

(73) Assignee: General Electric Company, Waukesha, WI (US)

(21) Appl. No.: 08/475,719

(22) Filed: Jun. 7, 1995

(51) Int. Cl.[7] ..... A61B 5/055

(52) U.S. Cl. ..... 600/410; 324/309; 600/420

(58) Field of Search ..... 128/653.2, 653.3, 128/653.4, 654; 324/307, 309; 600/410, 419, 420, 431

(56) References Cited

U.S. PATENT DOCUMENTS 5,271,401 * 12/1993 Fishman .
5,307,014 4/1994 Laub ..... 324/306
5,337,749 * 8/1994 Shimizu .
5,357,959 * 10/1994 Fishman .
5,419,325 * 5/1995 Dumoulin et al. .
5,499,629 * 3/1996 Kerr et al. .

OTHER PUBLICATIONS

Purdy et al, "The Design of Variable Tip Angle Slab Selection (TONE) Pulses for Improved 3–D MR Angiography", Book of Abstracts of SMRM, vol. 1, p. 882 (1992).
Middleton et al, "MR Imaging with Hyperpolarized $^3$He Gas", Magnetic Resonance in Medicine, vol. 330, pp. 271–275 (1995).
Conolly et al, "Prepolarized MRI with a Periodic Bias Field", Proceedings of the SMRM, vol. 3, p. 750 (1994).
Scott et al, "Body Noise Feasibility Limits of PMRI", Proceedings of the SMRM, vol. 2, p. 1083 (1994).
Mugler et al, "Shaping the Signal Response During the Approach to Steady State in Three–Dimensional Mag–Prep, Rapid G–E Imaging Using Variable Flip Angle", Mag. Reson. in Medicine, vol. 28, pp. 165–185 (1992).
Magele et al, "The Effects of Linearly Increasing Flip Angles on 3D Inflow MR Angiography", Mag. Reson. in Medicine, vol. 31, pp. 561–566 (1994).

* cited by examiner

*Primary Examiner*—Bernarr Earl Gregory
(74) *Attorney, Agent, or Firm*—Erwin F. Berrier, Jr.; John H. Pilarski; James O. Skarsten

(57) ABSTRACT

A method and apparatus is provided for generating an MR image of a structural portion of a subject, the portion lying within a hypothetical imaging volume. A specified level of hyperpolarized magnetization is provided within the imaging volume, and a series of MR pulse sequences are applied to the imaging volume to generate respective corresponding MR data signals, each pulse sequence comprising a number of magnetic field gradient pulses and an excitation pulse, and having an associated flip angle determined by the excitation pulse. The associated flip angles of successive pulse sequences are progressively increased to maintain the signal strength of the corresponding MR data signals at a substantially constant level. Acquired MR data signals are cumulatively processed to provide an image of the structural portion.

9 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HYPERPOLARIZED MR IMAGING USING PULSE SEQUENCE WITH PROGRESSIVELY INCREASING FLIP ANGLE

BACKGROUND OF THE INVENTION

The invention disclosed and claimed herein is generally directed to a technique for magnetic resonance (MR) imaging, wherein a hyperpolarized noble gas or other agent is used to provide the population of magnetized spins or nuclei required for imaging.

The hyperpolarized magnetization technique has been found to be very useful in increasing the signal to noise ratio in certain MR imaging applications. Such applications include imaging of the lungs or other organ or tissue of a subject, wherein the structure to be imaged is proximate to cavities or air spaces. In accordance with one such application of the hyperpolarization technique, a noble gas such as optically pumped Helium-3 or Xenon-129 is hyperpolarized externally to the subject, and then introduced into the cavities or air spaces, such as by inhaling into the lungs. The magnetization of the hyperpolarized gaseous agent is substantially greater than the magnetization predicted by the Boltzmann distribution at the magnetic field strength and temperature of the imaging situation. Accordingly, the strength of acquired MR data signals, used to construct an MR image, tends to be substantially greater than for more well known MR techniques, wherein the magnetized spin population is provided by applying a very strong static or main magnetic field to the subject. Hyperpolarized magnetization is described, for example, in an article entitled "MR Imaging With Hyperpolarized $^3$He Gas", Middleton et al, published in Magnetic Resonance in Medicine, Vol. 33, No. 2, pp. 271–275 (1995).

In alternative implementations of the hyperpolarization technique, the requisite level of magnetization is provided by hyperpolarizing body structure, blood or other body fluid of the subject, as described hereinafter in greater detail.

In the hyperpolarization technique, as in other MR methods, a succession of RF excitation pulses are directed into a volume enclosing the portion of the subject to be imaged. The excitation pulses, together with corresponding magnetic gradient fields, act to generate the MR data signals for imaging. Each excitation pulse diminishes the hyperpolarized magnetization. However, after introduction into the subject, there is no mechanism available to restore the hyperpolarized magnetization lost by successive RF excitation, resulting in substantial reduction in the strength of later-acquired MR data signals. Instead, the longitudinal (T1) relaxation of the magnetization in the patient is to the Boltzmann (rather than hyperpolarized) value, which is much smaller, and can often be considered negligible.

SUMMARY OF THE INVENTION

The invention is directed to a method for providing an MR image of a selected structural portion of a subject, the portion lying within a hypothetical imaging volume. The method comprises introducing a quantity of a magnetically hyperpolarized agent into the subject, proximate to the portion to be imaged, and applying a series of pulse sequences to the imaging volume to generate successive corresponding MR data signals. Each sequence comprises a number of gradient localization pulses and RF excitation pulses. The excitation pulse, which tips longitudinal magnetization into the transverse plane, has an associated flip angle. The associated flip angles are progressively increased to maintain the signal strength of the successive MR data signals at a substantially constant level. After acquisition, the MR data signals are processed to provide the desired image of the structural portion.

In a preferred embodiment of the invention, which neglects T1 relaxation (since the equilibrium magnetization is usually negligible compared to the hyperpolarized value), flip angle is increased by recursively setting the flip angle associated with a given pulse sequence to the inverse sine function of the tangent of the flip angle of the sequence just preceding the given pulse sequence in the series. Such embodiment is considered to simplify the task of progressively increasing the flip angles. In an imaging arrangement wherein the hyperpolarized and equilibrium magnetizations are comparable, the recursive relationship can be easily extended to include T1-relaxation.

It is anticipated that an embodiment of the invention will be particularly useful in imaging body structure such as lungs or heart related cardiac tissue, which surrounds or is proximate to cavities or air spaces which may receive a hyperpolarized gaseous agent. It is further anticipated that the invention will also be useful in imaging structure relating to blood or other fluid if a hyperpolarized agent is dissolved therein. Alternatively, the agent could comprise a quantity of blood or other fluid taken from a subject, externally hyperpolarized, and then reintroduced into the subject.

An object of the invention is to provide an MR imaging arrangement using hyperpolarized magnetization, wherein the signal strength of successive acquired MR data signals is maintained at a substantially constant level.

Another object is to provide an imaging arrangement of the above type, wherein the flip angle of each successive MR sequence is selectively increased over the preceding flip angle.

These and other objects of the invention will become more readily apparent from the ensuing specification, taken together with the accompanying drawings.

DETAILED DESCRIPTION OF THE PREFERRED EMBODIMENT

Figure 1:
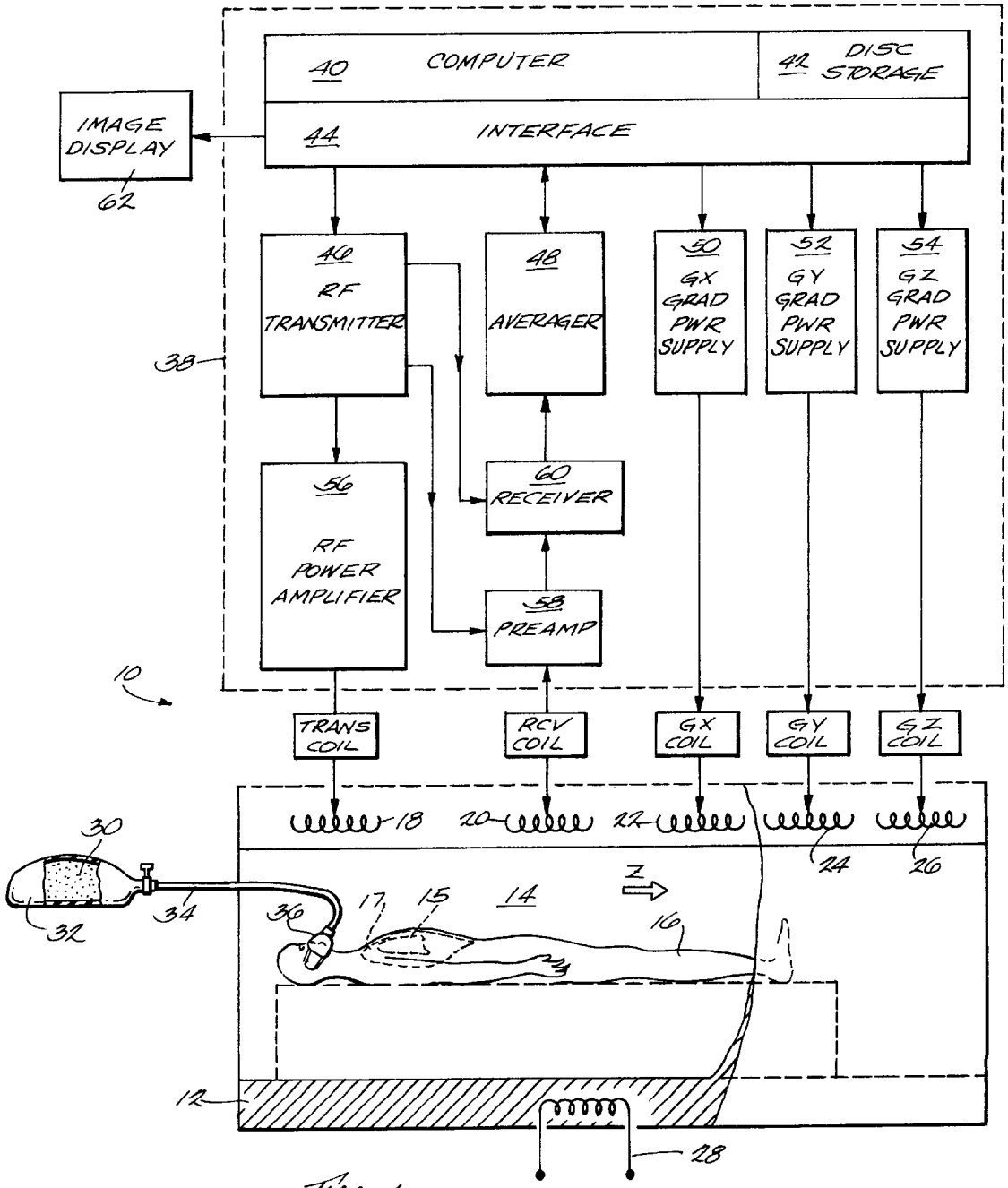
FIG. 1 is a diagram showing the principal components of an MR imaging system, for use in connection with an embodiment of the invention.

FIG. 1 shows the principal components of a conventional MR imaging system, as modified in accordance with the present invention. System 10 includes an imaging structure 12, which may be of tubular configuration and is provided with a bore 14 disposed to supportably receive a patient or other subject 16 of MR imaging. It is desired to obtain an image of a body portion 15 such as the lungs of subject 16, contained in a hypothetical imaging volume 17, or other body portion suitable for imaging by means of the hyperpolarized technique.

MR system 10 further includes a transmit or RF excitation coil 18, a receive coil 20, $G_x$, $G_y$ and $G_Z$ gradient coils 22, 24 and 26, respectively, and static field coil 28. Each of the coils 18 and 22–28 is incorporated into structure 12 so that when energized, they respectively project magnetic fields into bore 14 and subject 16. Receive coil 20 is likewise incorporated into structure 12, to detect MR signals generated within subject 16. Operation of respective coils 18–28 is described hereinafter in greater detail.

As is well known, and as indicated above, MR imaging requires a very large population of magnetized spins, which are initially aligned or orientated along the axis of the bore 14 of structure 12, shown in FIG. 1 as the Z-axis. As was also indicated, the hyperpolarized technique of MR imaging, unlike other techniques, does not require a strong static magnetic field in the bore 14, such as a field on the order of 0.2–4 Tesla, to align spins of the body structure of subject 16. Instead, the population of magnetized spins needed for MR imaging is provided by introducing a hyperpolarized agent 30, such as noble gas Helium-3 or Xenon-129, into the imaging volume 17 of subject 16 so that the agent 30 is close to the body portion 15. It should be noted that a static magnetic field (which may be weak) will still be required to enable the imaging experiment. Such field is provided by coil 28.

To image an organ such as the lungs, the hyperpolarized gas 30 is usefully conducted from a container 32 to the nose or mouth of subject 16, by means of a hose 34 and mask 36 and inhaled into the subject's lungs. The hyperpolarized gas then fills the air spaces around the lung tissue to be imaged. It is anticipated that other techniques will readily occur to the those of skill in the art for conducting hyperpolarized agent 30 into proximate relationship with other body parts suitable for imaging by means of hyperpolarized imaging, or into blood pool or other fluid.

Techniques for producing a hyperpolarized gas 30 externally from subject 16 are known to those of skill in the art. For example, a technique for hyperpolarizing Helium-3 gas, for use as agent 30, is taught in the Middleton et al article, MRM 33:271–275 (1995), referred to above.

Coil 28 shown in FIG. 1 is operated to generate a static magnetic field in bore 14 which is directed along the Z-axis, and is on the order of 300 Gauss or higher. Such field can be weak in comparison with the 0.2–4 Tesla field of other MR imaging arrangements.

In the MR imaging process a series of pulse sequences are generated by selectively energizing transmit coil 18 and gradient coils 22, 24 and 26. Coil energizing is controlled by MR system electronics 38, described hereinafter. Coil 18 is energized during a sequence to project an RF excitation pulse into bore 14, including imaging volume 17, to urge the hyperpolarized spins of gas 30 out of alignment with the Z-axis. The gradient coils are energized during the sequence, as described hereinafter, to project respective gradient pulses into bore 14, and to thereby generate a data signal. The data signal contains information representing a view of the structure 15 to be imaged, and is detected by coil 20, as stated above. As is known in MR imaging, the number of pulse sequences in a series may be on the order of 128 or 256, to provide sufficient views for use in constructing an image.

In addition to RF excitation and gradient pulses, each pulse sequence has an associated flip angle. As is known, flip angle is determined by the amplitude and the time duration of the RF excitation pulse of the sequence.

As stated above, the excitation pulse of each successive pulse sequence diminishes the hyperpolarized longitudinal magnetization $M_z$. Thus, $M_z$ is a function of i, where i represents the number of the pulse sequence in the series. If the views are acquired sequentially, it also represents the number of the view. In the system shown in FIG. 1, the hyperpolarized magnetization is assumed to be substantially greater than Boltzmann magnetization. Given this assumption, $M_z(i)$, the magnetization after the ith pulse sequence, is related to the flip angle thereof, $\theta(i)$, by the expression $M_z(i)=M_z(i-1)$ cosine $\theta(i)$.

S(i), the signal strength of the data signal acquired by the ith pulse sequence, and which can represent the ith view, can significantly decrease as the hyperpolarized magnetization $M_z$ is reduced. In accordance with the invention, to maintain S(i) of successive MR data signals at a substantially constant strength level, the flip angle associated with successive pulse sequences is progressively increased, according to a specified relationship. Moreover, if $M_z$ is assumed to be much greater than Boltzmann magnetization, as stated above, $\theta_i$, the flip angle of the first pulse sequence, may be set to a low value such as 5 degrees. (In general the more views that will be acquired, the lower the initial flip angle should be set.) Then, each succeeding flip angle $\theta(i)$ can be readily computed as the inverse sine function of the tangent of the immediately preceding flip angle, that is:

$$\theta(i)=\sin^{-1}[\tan\theta(i-1)] \qquad \text{Eqn. (1)}$$

Eqn. (1) can alternatively be expressed as the relationship $\theta(i)=\tan^{-1}[\tan\theta(i-1)/\sqrt{1-\tan^2\theta(i-1)}]$.

The recursion relation of Equation 1 may be solved in closed form, that is:

$$\theta_i=\tan^{-1}[\tan\theta_1/\sqrt{1-(i-1)\tan^2\theta_1}] \qquad \text{Eqn. (2)}$$

where $\theta_1$ is the flip angle of the first RF pulse. This relation gives further insight into choosing the initial flip angle. $\theta_1$ should be chosen to be as large as possible, subject to the constraint that the argument of the square root is never negative. Thus we choose $\theta_i$, as follows:

$$\theta_1 \leqq \tan^{-}\sqrt{1/(N-1)} \qquad \text{Eqn. (3)}$$

where N is the total number of pulse sequences in the series.

Figure 2:
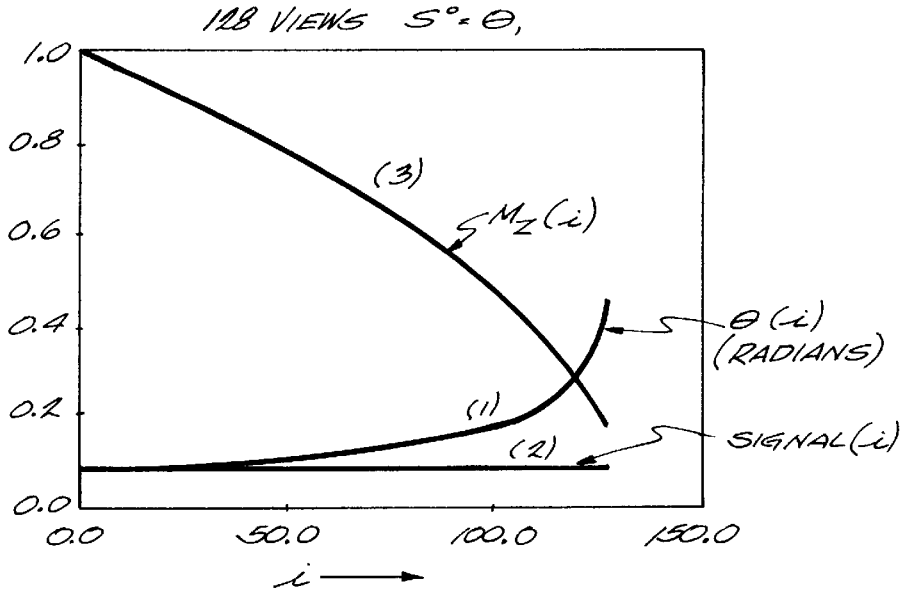
FIG. 2 is a graph which respectively depicts flip angle, the level of hyperpolarized magnetization, and the level of acquired MR data signals, each as a function of a view number, for use in illustrating an embodiment of the invention.

FIG. 2 graphically illustrates the above findings. Curve (1) shown in FIG. 2 comprises a plot of the above function $\theta(i)$ versus i, for an initial flip angle $\theta_i$ of 5 degrees and 128 views. As stated above, i is the number of the pulse sequence in the series. Curve (2) of FIG. 2 shows the signal strength level S(i) remaining substantially constant as i increases, notwithstanding the continuing decline of magnetization $M_z(i)$ shown by curve (3).

Figure 3:
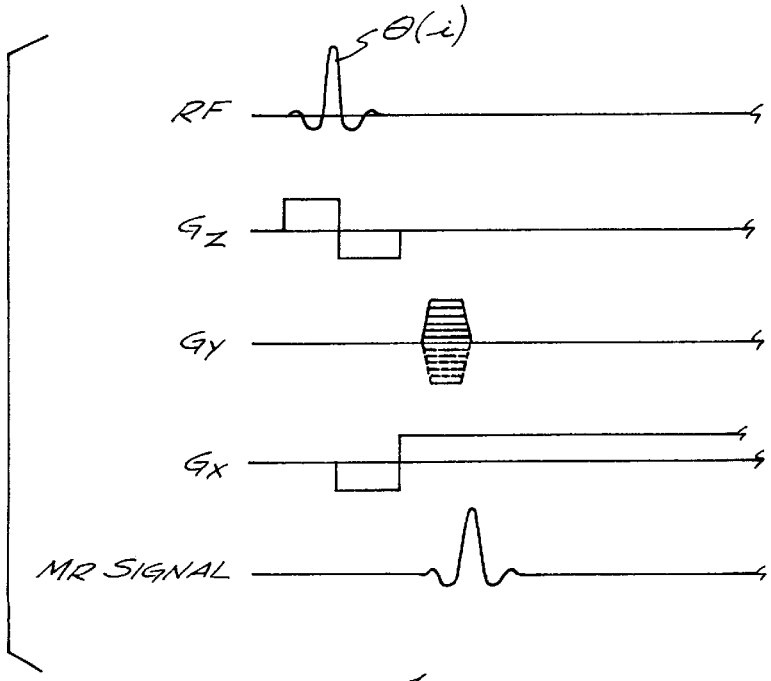
FIG. 3 shows an MR pulse sequence for an embodiment of the invention.

Referring to FIG. 3, there is shown a pulse sequence for an embodiment of the invention, which includes an RF excitation pulse. For the ith pulse sequence, the amplitude and duration of the excitation pulse are set with respect to each other to provide a flip angle $\theta(i)$ in accordance with Equation (1), above.

FIG. 3 further shows $G_z$, $G_y$ and $G_z$ gradient pulses, usefully comprising the slice-select, phase encoding and frequency encoding pulses, respectively, of the pulse sequence which is well know to those of skill in the art as spin warp imaging. This sequence is described, for example, in an article entitled "Spin Warp NMR Imaging and Applications to Human Whole -Body Imaging", Edelstein, et al, Phys. Med. Biol. 25:751–756 (1980). In the spin warp technique, the amplitude of the $G_y$ gradient is changed for each successive pulse sequence, to provide the MR data signals, each representing a different view. A pulse sequence generates the corresponding MR data signal by gradient reversal, i.e., by reversing the polarity of the $G_x$ gradient. The gradient pulses also serve to spatially localize the imaging information provided by the respective MR data signals.

The pulse sequence for the invention may further include additional pulses, not shown in FIG. 3, to improve the quality of acquired data signals and the image constructed therefrom. For example, the sequence could be provided with a rewinder pulse, as used in the sequence known in The art as Gradient Recalled Echo. (GRE) The GRE sequence is shown, for example, in a review entitled "Fast MRI Imaging", edited by R. R. Edelman and J. R. Hesselink, in the book *Clinical MRI,* Ch. 5, published by W. B. Saunders, 1990.

Referring further to FIG. 1, there is shown MR system 10 further including MR system electronics 38, comprising components for selectively energizing coils 18, 22, 24 and 26, and for processing the MR data signals detected by receive coil 20. System electronics 38 includes a general purpose computer 40, which is interactively coupled to a disc storage 42 and an interface 44. An RF transmitter 46, a signal averager 48, and gradient power supplies 50, 52 and 54 are respectively coupled to computer 40 through interface 44 to enable computer 40 to control the respective operations thereof. Gradient power supplies 50, 52 and 54 respectively energize the $G_x$, $G_y$ and $G_z$ gradient coils 22, 24 and 26. RF transmitter 46 is coupled through an RF power amplifier 56 to energize transmit or excitation coil 18. Computer 40, acting through interface 44, selectively couples signals to the respective coil energizing components to generate pulse sequences, such as the sequence described above in connection with FIG. 3.

Computer 40 also controls the duration of an RF pulse generated by transmitter 46, as well as the amplification level of amplifier 56. Thus, computer 40 can operate coil 18 to generate an excitation pulse which will provide a flip angle in accordance with Equation (1) or Equation (2), above.

MR electronics 38 further includes a low noise pre-amplifier 58, which receives and pre-amplifies respective MR data signals detected by coil 20. Pre-amplified data signals are applied to a receiver 60 for further amplification, direction and filtering. By means of the receiver 60, the signals are digitized for averaging by signal averager 48 and then coupled to computer 40 through interface 44.

Computer 40 performs data processing functions with respect to received MR data signals, such as Fourier transformation and image reconstruction. After processing of the received data MR signals has been completed, computer 40 couples a corresponding image reconstruction signal to a display 62 to provide an image of structure 15 in viewable form.

As is well known, a single coil can be substituted for transmit coil 18 and receive coil 20. In such modification, a switching mechanism is provided to alternately couple amplifier 56 and preamplifier 58 to such coil.

In the embodiment of the invention described above, successive values of flip angle are computed by means of Equation (1) or Equation (2), which does not take into account changes of magnetization resulting from T1 relaxation. However, in a modification of the invention, such effect could be taken into account in computing progressively increasing values of flip angle.

It is anticipated that the invention could employ pulse sequences using both segmented and non-segmented K-space.

In a modification of the invention of particular interest in imaging blood and body structure pertaining thereto, the hyperpolarized agent comprises a quantity of blood or other fluid of the subject 16. In accordance with a technique referred to in commonly assigned U.S. patent application Ser. No. 08/264283, entitled "Magnetic Resonance (MR) Angiography in a Low-Field Imaging Magnet", filed Jun. 17, 1994 by Charles Dumoulin and Robert David, an amount of blood is removed from the subject by conventional means. The removed blood is then hyperpolarized, by placing it in a very strong static magnetic field, such as on the order of 1–10 Tesla. The hyperpolarized blood is then reinserted into a blood vessel at a selected location of the subject 16, to provide the requisite level of hyperpolarized magnetization for imaging as described above.

In a further modification, the coil used as coil 28 of FIG. 1 is capable of applying a strong magnetic pulse to subject 16 in bore 14, to hyperpolarize the portion of the body structure of subject 16 which is to be imaged. The pulsed polarizing field can be very inhomogeneous. This approach to generating the required level of hyperpolarized magnetization within subject 16 is described, for example, in an article entitled "Prepolarized MRI with a Periodic Bias Field", Conolly, Morgan, Scott and Macovski, published in Proceedings of the Society of Magnetic Resonance, p. 750, Vol. 3, 1994.

Obviously, many other modifications and variations of the present invention are possible in light of the above teachings. It is therefore to be understood that within the scope of the disclosed inventive concept, the invention may be practiced otherwise than as specifically described.

What is claimed is:

1. A method for providing a magnetic resonance (MR) image of a structural portion of a subject, the portion lying within a hypothetical imaging volume, said method comprising the steps of:

introducing a quantity of magnetically hyperpolarized agent into said subject proximate to said structural portion;

successively applying a series of MR pulse sequences to said imaging volume over a specified period of time, to generate respective corresponding MR data signals, wherein each sequence comprises a number of magnetic field gradient pulses and an excitation pulse, has an associated number representing its position in said series, and has an associated flip angle determined by its excitation pulse;

computing the value of a first flip angle associated with the first pulse sequence in said series;

non-recursively computing the associated flip angle of each successive pulse sequence in said series, following said first sequence, from said first flip angle value and from a non-linear function of said sequence position numbers, each of said non-recursively computed flip angles being successively increased to maintain the signal strength of said corresponding MR data signals at a substantially constant level over said specified time period; and processing said corresponding MR data signals to provide said image of said structural portion.

2. The method of claim 1 wherein:

the first pulse sequence in said series has a flip angle $\theta_1$ of specified value, and $\theta(i)$, the flip angle associated with the ith pulse sequence in the series, has a value given by the relationship $\theta(i)=\tan^{1}(\tan\theta_1\sqrt{1-(i-1)\tan^2\theta_1})$, where i is a positive integer between 2 and N, and N is the total number of pulse sequences in the series.

3. The method of claim 1 wherein:

said structural portion comprises structure within said subject proximate to a cavity disposed to receive said hyperpolarized agent.

4. The method of claim 3 wherein:

said structural portion comprises structure of the lungs of said subject.

5. The method of claim 3 wherein:

said structural portion comprises cardiac structure of said subject.

6. The method of claim 1 wherein:

said hyperpolarized agent is the noble gas Helium-3.

7. The method of claim 1 wherein:

said hyperpolarized agent is the noble gas Xenon-129.

8. The method of claim 1 wherein:

said hyperpolarized agent comprises a quantity of blood which has been removed from said subject, hyperpolarized externally from said subject, and then reinserted into said subject at a specified location.

9. Apparatus for providing a magnetic resonance (MR) image of a structural portion of a subject, the portion lying within a hypothetical imaging volume, said apparatus comprising:

means for introducing a quantity of magnetically hyperpolarized agent into said subject proximate to said structural portion;

means for successively applying a series of MR pulse sequences to said imaging volume over a specified period of time, to generate respective corresponding MR data signals, wherein each sequence comprises a number of magnetic field gradient pulses and an excitation pulse, has an associated number representing its position in said series, and has an associated flip angle determined by the its excitation pulse;

means for computing the value of a first flip angle associated with the first pulse sequence in said series;

means for non-recursively computing the associated flip angle of each successive pulse sequence in said series, following said first sequence, from said first flip angle value and from a non-linear function of said sequence position numbers, each of said non-recursively computed flip angles being successively increased to maintain the signal strength of said corresponding MR data signals at a substantially constant level over said specified time period; and means for processing said corresponding MR data signals to provide said image of said structural portion.

* * * * *